(12) United States Patent
Liu et al.

(10) Patent No.: US 8,818,507 B2
(45) Date of Patent: Aug. 26, 2014

(54) CORONARY VEIN DIMENSIONAL SENSOR AND FIXATION APPARATUS

(75) Inventors: Lili Liu, Maple Grove, MN (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 925 days.

(21) Appl. No.: 12/431,301

(22) Filed: Apr. 28, 2009

(65) Prior Publication Data

US 2009/0299427 A1 Dec. 3, 2009

Related U.S. Application Data

(60) Provisional application No. 61/056,285, filed on May 27, 2008.

(51) Int. Cl.
*A61N 1/362* (2006.01)
*A61B 5/11* (2006.01)
*A61N 1/05* (2006.01)
*A61B 5/02* (2006.01)
*A61N 1/365* (2006.01)
*A61B 5/00* (2006.01)
*A61B 5/0215* (2006.01)

(52) U.S. Cl.
CPC .............. *A61N 1/057* (2013.01); *A61B 5/1107* (2013.01); *A61N 1/36578* (2013.01); *A61N 2001/0585* (2013.01); *A61B 5/686* (2013.01); *A61B 2562/0261* (2013.01); *A61B 5/02028* (2013.01); *A61N 1/3627* (2013.01); *A61B 5/02* (2013.01); *A61B 5/0215* (2013.01)
USPC .............................. 607/17; 607/122; 600/481

(58) Field of Classification Search
USPC .............................. 607/122, 126, 17; 600/481
See application file for complete search history.

(56) References Cited

U.S. PATENT DOCUMENTS

| | | | |
|---|---|---|---|
| 4,686,987 A | 8/1987 | Salo et al. | |
| 5,324,326 A | 6/1994 | Lubin | |
| 5,356,883 A | 10/1994 | Kuo et al. | |
| 5,423,883 A | 6/1995 | Helland | |
| 5,464,434 A | 11/1995 | Alt | |
| 6,078,835 A | 6/2000 | Hedberg et al. | |
| 6,277,078 B1 | 8/2001 | Porat et al. | |
| 6,278,894 B1 | 8/2001 | Salo et al. | |
| 6,512,949 B1 * | 1/2003 | Combs et al. | 600/547 |
| 6,580,946 B2 | 6/2003 | Struble | |
| 6,892,095 B2 | 5/2005 | Salo | |
| 6,909,919 B2 | 6/2005 | Jain et al. | |
| 6,934,586 B2 | 8/2005 | Struble et al. | |
| 6,970,742 B2 | 11/2005 | Mann et al. | |
| 6,976,967 B2 | 12/2005 | Dahl et al. | |
| 7,195,594 B2 | 3/2007 | Eigler et al. | |

(Continued)

FOREIGN PATENT DOCUMENTS

WO WO2008150590 12/2008

*Primary Examiner* — Alyssa M Alter
(74) *Attorney, Agent, or Firm* — Faegre Baker Daniels LLP

(57) ABSTRACT

A system and method for estimating a hemodynamic performance parameter value of a patient's heart. The system includes a pulse generator and a medical electrical lead implanted partially within a coronary vein of the heart. The lead includes at least one sensor located within the coronary vein configured to generate a signal indicative of at least one dimensional parameter of the coronary vein. Changes in the dimensional parameter during one or more cardiac cycles are measured. The hemodynamic performance parameter is estimated based on the change in the dimensional parameter of the coronary vein.

12 Claims, 4 Drawing Sheets

(56) References Cited

U.S. PATENT DOCUMENTS

| | | |
|---|---|---|
| 7,200,439 B2 | 4/2007 | Zdeblick et al. |
| 7,206,637 B2 | 4/2007 | Salo |
| 7,233,821 B2 | 6/2007 | Hettrick et al. |
| 7,269,460 B2 | 9/2007 | Chinchoy |
| 7,272,443 B2 | 9/2007 | Min et al. |
| 7,483,743 B2 | 1/2009 | Mann et al. |
| 2001/0010009 A1 | 7/2001 | Bakels et al. |
| 2003/0167024 A1 | 9/2003 | Imran et al. |
| 2003/0181938 A1 | 9/2003 | Roth et al. |
| 2004/0049255 A1* | 3/2004 | Jain et al. .................. 607/122 |
| 2004/0210268 A1 | 10/2004 | Stubbs |
| 2005/0149156 A1* | 7/2005 | Libbus et al. .............. 607/119 |
| 2006/0089679 A1 | 4/2006 | Zhu et al. |
| 2006/0276849 A1 | 12/2006 | Carlson et al. |
| 2007/0088221 A1 | 4/2007 | Stahmann |
| 2007/0112388 A1 | 5/2007 | Salo |
| 2007/0142732 A1 | 6/2007 | Brockway et al. |
| 2008/0234556 A1 | 9/2008 | Brooke et al. |
| 2008/0281367 A1 | 11/2008 | Zhang et al. |

* cited by examiner

CORONARY VEIN DIMENSIONAL SENSOR AND FIXATION APPARATUS

CROSS-REFERENCE TO RELATED APPLICATION

This application claims the benefit under 35 U.S.C §119 of U.S. Provisional Application No. 61/056,285, filed on May 27, 2008, entitled "Coronary Vein Dimensional Sensor And Fixation Apparatus," which is herein incorporated by reference in its entirety.

This application is related to U.S. application Ser. No. 12/256,203, filed on Oct. 22, 2008, entitled "Coronary Vein Hemodynamic Sensor," which is herein incorporated by reference in its entirety.

TECHNICAL FIELD

The present invention relates to a method and system for estimating and monitoring cardiac hemodynamic performance, and in particular, for estimating hemodynamic performance utilizing one or more sensing elements coupled to a lead implanted in a coronary vein.

BACKGROUND

Various measures have been identified for estimating and evaluating reduced cardiac function. Such measures include left ventricular pressure (LVP), which can be useful in estimating and evaluating cardiac hemodynamic performance. Direct measurement of LVP requires locating one or more pressure sensors directly in the left ventricle, which can be technically and clinically challenging.

SUMMARY

According to some embodiments, the present invention is a cardiac rhythm management system including a cardiac lead adapted to be delivered to a target location within a coronary vein having an inner wall, the cardiac lead including a strain sensing element coupled to the distal end of the lead body, and a pulse generator including a signal processing unit operatively coupled to the strain sensing element. The cardiac lead includes an elongated lead body including a distal end, at least one electrode coupled to the lead body, and at least one conductor extending within the lead body operatively coupled to the at least one electrode. The strain sensing element is configured to radially expand against and frictionally engage the inner wall of the coronary vein, and is further configured to generate an output signal indicative of changes in a localized inner dimension of the coronary vein during a cardiac cycle. The pulse generator includes a signal processing unit configured to receive the output signal from the strain sensing element and to estimate a measure of hemodynamic performance therefrom.

According to various embodiments, the strain sensing element is operable as a fixation mechanism for chronically securing and stabilizing the distal end of the lead within the coronary vein. Additionally, the strain sensing element is configured to deform in response to the changes in the inner dimension of the coronary vein during the cardiac cycle. The output signal generated by the strain sensing element is proportional to the deformation of the strain sensing element.

According to various embodiments, the strain sensing element can include a strain gauge sensor, a piezoelectric sensor, or an optical sensor. According to various other embodiments, the strain sensing element includes at least two electrodes adapted to sense a change in localized impedance within the coronary vein during the cardiac cycle.

According to some embodiments the present invention is a method of estimating cardiac hemodynamic performance including: implanting a medical electrical lead including at least one strain sensing element partially within a coronary vein of a patient's heart; generating a signal indicative of at least one dimensional parameter of the coronary vein using the strain sensing element; and estimating a hemodynamic performance parameter as a function of changes in the signal during each of a plurality of cardiac cycles. According to further embodiments, the change in the dimensional parameter detected is a change $\Delta D_{max-min}$ in a localized inner diameter of the coronary vein.

According to other embodiments, the present invention is a method of estimating cardiac hemodynamic performance including delivering a lead including a strain sensing element adapted to be transitioned from a collapsed configuration to an expanded configuration to a target location within a coronary vein having an inner wall and an inner diameter, and transitioning the strain sensing element from the collapsed configuration to the expanded configuration such that the strain sensing element contacts and bears against the inner wall of the coronary vein, securing and stabilizing the lead within the coronary vein. The method further includes detecting a change in a localized inner diameter of the coronary vein in response to deformation of the strain sensing element during a cardiac cycle, and estimating a change in a hemodynamic performance parameter as a function of the change in the inner diameter of the coronary vein over a plurality of cardiac cycles. According to further embodiments, the hemodynamic performance parameter is any one of a change in left ventricular pressure, a change in left ventricular end systolic pressure, a change in left ventricular diastolic pressure, a change in maximum left ventricular contractility, or a change in minimum left ventricular wall contractility.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
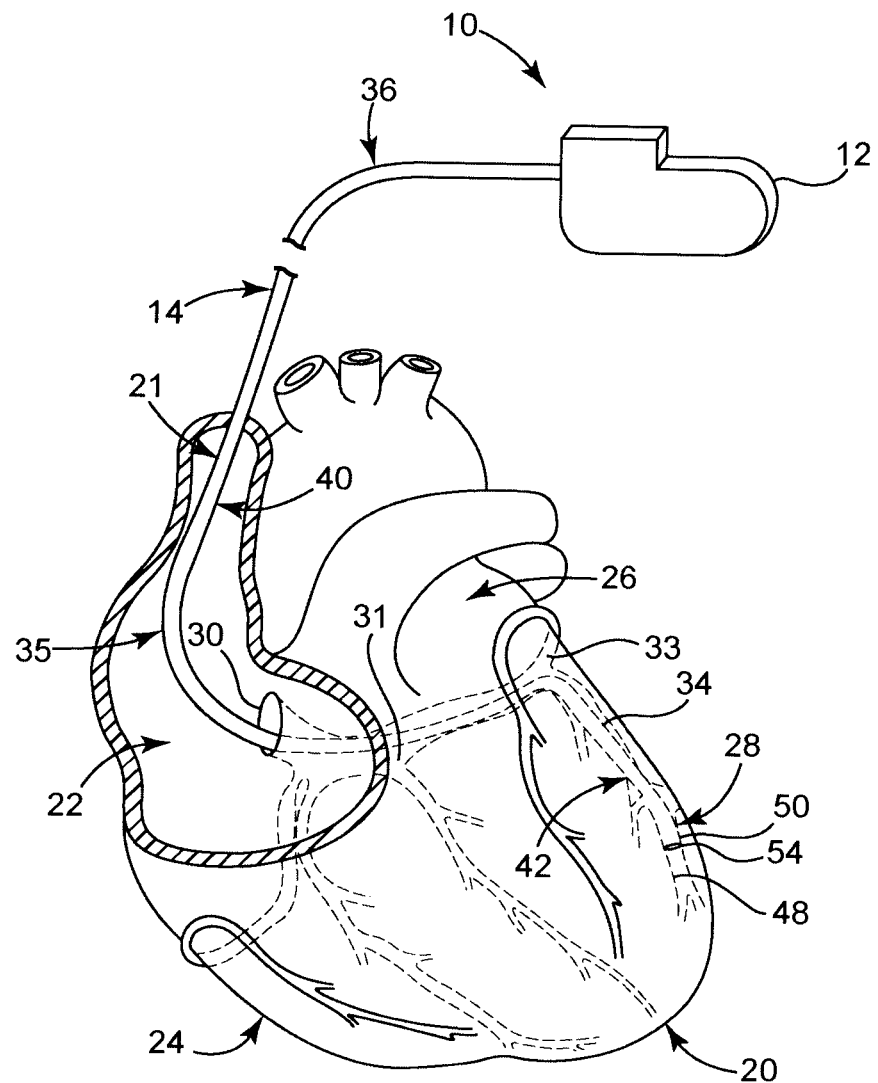
FIG. 1 is a schematic view of a cardiac rhythm management system including a pulse generator and a lead according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives failing within the scope of the invention as defined by the appended claims.

DETAILED DESCRIPTION

FIG. 1 is a schematic view of a cardiac rhythm management system 10 including a pulse generator 12 coupled to a lead 14 deployed in a coronary vein of a patient's heart 20 from a superior vena cava 21. As is known in the art, the pulse generator 12 is typically implanted subcutaneously at an implantation location in the patient's chest or abdomen. As shown, the heart 20 includes a right atrium 22 and a right ventricle 24, a left atrium 26 and a left ventricle 28, a coronary sinus ostium 30 in the right atrium 22, a coronary sinus 31, and various coronary veins including a great cardiac vein 33 and an exemplary branch coronary vein 34.

As shown in FIG. 1, the lead 14 includes an elongate body 35 defining a proximal region 36 and a distal region 40. The distal region 40 has a distal end portion 42 terminating in a distal tip 48. The lead 14 includes at least one electrode 50 operatively coupled to at least one conductor extending through the lead body 35. In the embodiment illustrated in FIG. 1, the distal region 40 is guided through the superior vena cava 21, the right atrium 22, the coronary sinus ostium 30, and the coronary sinus 31, and into the coronary vein 34, with the distal end portion 42 positioned therein. The illustrated position of the lead 14 may be used, for example, for sensing physiologic parameters and delivering a pacing and/or defibrillation stimulus to the left side of the heart 20. The lead 14 may also be partially deployed in other coronary veins such as the great cardiac vein 33 or other branch vessels for providing therapy to the left side (or other portions) of the heart 20.

The lead 14 is overall sized and shaped to provide the desired functionality according to the particular needs of the patient. In various embodiments, the lead 14 may be configured in substantially the same manner as conventional coronary venous leads for cardiac resynchronization therapy, bi-ventricular pacing, and the like, modified as described herein to facilitate sensing and measuring coronary vein dimensional parameters. In various embodiments, the lead 14 may be sized and configured to partially occlude a portion of the coronary vein 34 to effectively form a chamber in which at least one electrode 50 is positioned when implanted. In other embodiments, however, the size and configuration of the lead 14 are selected such that it does not significantly occlude the coronary vein 34.

The pulse generator 12 may be any implantable medical device known in the art or later developed, for delivering an electrical therapeutic stimulus to the patient. In one embodiment, the pulse generator 12 is a pacemaker. In one embodiment, the pulse generator 12 is a cardiac resynchronization (CRT) device configured for bi-ventricular pacing and sensing. In another embodiment, the pulse generator 12 is an implantable cardiac defibrillator. In still other exemplary embodiments, the pulse generator 12 includes combinations of pacing, CRT, and defibrillation capabilities. As will be appreciated, the pulse generator 12 includes circuitry and components for providing the desired therapeutic functionality, including at least one processor for receiving and processing signals generated by one or more sensing elements on the lead 14.

According to various embodiments of the present invention, as further shown in FIG. 1, the lead 14 includes at least one strain sensing element 54 coupled to the distal end 42, which in the implanted position of FIG. 1 is also located in the coronary vein 34. As will be explained in greater detail below, in the illustrated embodiment, the sensing element 54 is configured to sense one or more dimensional parameters, e.g., volume, diameter, circumference, etc. of the coronary vein 34. As such, the sensing element 54 can be used to generate signals indicative of such dimensional parameters. Furthermore, when processed in the pulse generator 12 or elsewhere, these signals may be utilized to measure changes in the dimensional parameters during the cardiac cycle, and such measured changes can be utilized to estimate hemodynamic performance parameters, control patient therapy, and the like.

The coronary vein 34 will undergo dimensional changes during the cardiac cycle. In particular, the internal diameter D of the coronary vein 34 will generally decrease as the cardiac chambers fill during diastole. Similarly, the internal diameter D of the coronary vein 34 tends to increase as the internal pressure and blood flow within the coronary vein 34 increase during systole. As will be appreciated, changes in the internal diameter D of the coronary vein 34 results in corresponding changes in the localized internal volume V of the coronary vein 34. Thus, localized internal volume changes $\Delta V$ for the coronary vein 34 can be estimated by sensing and measuring the corresponding changes in internal diameter $\Delta D$ of the coronary vein 34. In other words, a comparison of the systolic internal diameter $D_{sys}$ of the coronary vein 34 with the diastolic internal diameter $D_{dia}$ of the coronary vein during a cardiac cycle will correlate well with the change in internal volume $\Delta V$ of the coronary vein 34 during the cardiac cycle.

Additionally, the change in coronary venous diameter $\Delta D$ during the cardiac cycle will correlate well with changes in LVP during the cardiac cycle, to substantially the same extent to which coronary venous pressure correlates with LVP, as disclosed in, for example, U.S. Pat. No. 6,666,826 to Salo, et al., which is incorporated herein by reference in its entirety. As is generally known, LVP is an important measure for evaluating the hemodynamic performance of the heart. Thus, the various embodiments of the present invention configured for sensing and measuring changes in localized coronary vein internal diameter can facilitate similar measurement and evaluation of hemodynamic performance without requiring direct measurement of LVP or coronary venous pressure. In other words, according to the various embodiments of the present invention, the coronary venous internal diameter changes during the cardiac cycle can be utilized to derive any of the hemodynamic performance parameters that can be derived by measuring coronary venous pressure and/or LVP.

Figure 2A:
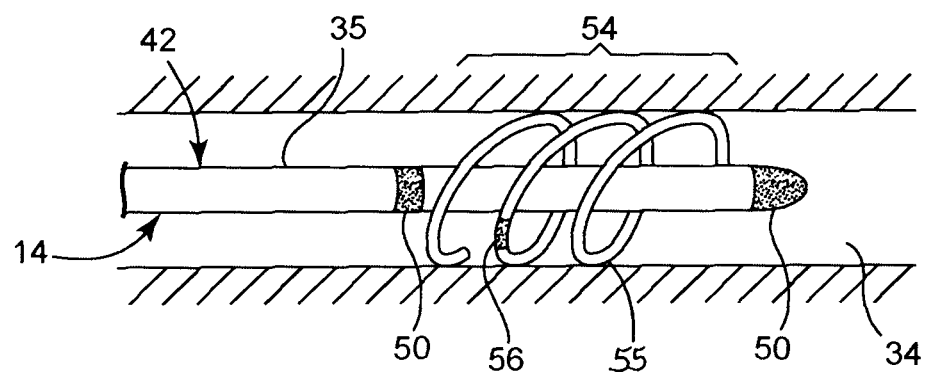
FIGS. 2A and 2B are schematic views of a distal end portion of a lead positioned in a coronary vein according to various embodiments of the present invention.
Figure 2B:
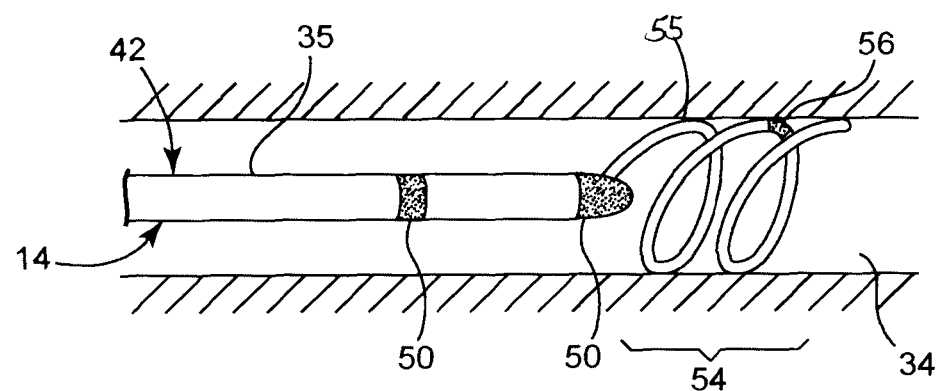

FIGS. 2A and 2B are schematic views of the distal end portion 42 of the lead 14 positioned in the coronary vein 34 according to some embodiments of the present invention. As shown in FIG. 2A, the strain sensing element 54 is coupled to the lead body 35 and is radially expandable to an outer diameter greater than the outer diameter of the lead body 35. The strain sensing element 54 can have any configuration suitable for providing the desired flexibility and an ability to be pre-biased to assume an expanded configuration such as shown in FIGS. 2A and 2B. In the illustrated embodiment, the strain sensing element 54 is in the form of a helical coil, and is adapted to expand radially to a diameter sufficient to contact and frictionally engage the inner wall of the coronary vein 34 to secure and stabilize the distal end 42 of the lead 14 in the coronary vein 34. Thus, the strain sensing element 54 also operates as a fixation mechanism for maintaining the lead 14 in the desired implanted position.

The strain sensing element 54 is configured to flex with the contraction and dilation of the coronary vein 34 during the cardiac cycle. In this manner, the strain sensing element 54 is responsive to changes in the inner diameter of the coronary vein 34 resulting from the systolic and diastolic action of the heart during the cardiac cycle, and further generates an output signal indicative of such changes in coronary vein diameter. The strain sensing element 54 is electrically coupled to a processor and/or circuitry within the pulse generator 12 (see FIG. 1) for facilitating detecting and measuring the changes in coronary vein diameter, as well as other dimensional parameters that can be derived therefrom (e.g., changes in localized coronary vein volume). The changes detected and measured in the dimensional parameter can be used to calculate the difference $\Delta D_{max-min}$ between the maximum coronary vein diameter $D_{max}$ (i.e., the diameter at the end of systole) and minimum coronary vein diameter $D_{min}$ (i.e., the diameter at the end of diastole). The difference $\Delta D_{max-min}$ between the maximum coronary vein diameter $D_{max}$ (i.e., the diameter at the end of systole) and minimum coronary vein diameter $D_{min}$ (i.e., the diameter at the end of diastole) will correlate to LVP and can be used to estimate cardiac hemodynamic performance. That is, cardiac hemodynamic performance can be estimated and evaluated based on $\Delta D_{max}$ derived from the strain sensing element 54.

According to various embodiments, the strain sensing element 54 includes an expandable member 55 and one or more strain sensors 56 coupled to the expandable member 55 and adapted to respond to the deformation of the sensing element 54 by sending a signal indicative of changes in a localized inner dimension of the coronary vein during a cardiac cycle. According to various embodiments, the expandable member 55 is configured to radially expand and bear against the inner walls of the vein in which the lead is deployed. The expandable member 55 can have any configuration known in the art such as, for example, a helix or a stent-like configuration. The expandable member 55 can be made from a shape memory material such as a Nitinol or another super elastic material having shape memory properties such that it is adapted to self-expand from a collapsed position suitable for delivery into the vein to an expanded position.

According to various embodiments, the strain sensor 56 is a strain gauge sensor configured to measure the change in electrical resistance in response to the deformation of the strain sensing element 54 during the contraction cycle of the heart. The change in electrical resistance measured by the strain gauge sensor correlates to the change between the maximum coronary vein diameter $D_{max}$ (i.e., the diameter at the end of systole) and minimum coronary vein diameter $D_{min}$ (i.e., the diameter at the end of diastole), and can be used to estimate cardiac hemodynamic function. In other embodiments, other strain gauge sensor configurations may be utilized.

According to one exemplary embodiment, the strain gauge sensor 56 is secured to the outer surface of or embedded within the strain expandable member 55. An exemplary strain gauge sensor 56 includes a flexible, backing material supporting a metallic foil circuit including two terminal ends. The circuit can be coupled to a first lead adapted to supply power to the circuit from a power source located within the pulse generator, and a second lead adapted to carry a signal indicative of a change in the inner diameter of the vein from the strain sensor to the signal processor within the pulse generator. As the expandable member 55 is deformed during the cardiac cycle, the foil circuit is deformed, causing the electrical resistance across the terminal ends of the circuit to change. The change in electrical resistance is proportional to the change in the inner diameter of the vein. A signal indicative of this change is sent via the second lead from the strain sensor 56 to the signal processor within the pulse generator.

According to another embodiment, the strain sensor 56 can be an optical sensor. Changes in the coronary vein diameter results in a change in the refractive index measured by the optical sensor. The change in refractive index is used to estimate and evaluate cardiac hemodynamic performance. The change in refractive index measured by the optical sensor correlates to the change between the maximum coronary vein diameter $D_{max}$ (i.e., the diameter at the end of systole) and minimum coronary vein diameter $D_{min}$ (i.e., the diameter at the end of diastole). According to one embodiment, the optical sensor can include at least one optical fiber embedded within the expandable member 55. For example, according to some embodiments, the expandable member 55 includes a lumen having a diameter sufficient to allow an optical fiber to be located inside the lumen. The optical fiber can be coupled to a first lead adapted to supply power to the optical fiber from a power source located within the pulse generator, and a second lead adapted to carry a signal indicative of a change in the inner diameter of the vein from the optical fiber to the signal processor within the pulse generator. Mechanical forces applied to the expandable member 55 including the optical fiber dynamically effects the detected optical characteristics thereby indicating changes in strain.

According to another exemplary embodiment, the strain sensor 56 can be a piezoelectric sensor. According to some embodiments, the piezoelectric sensor can be secured to the outer surface or embedded within the expandable member 55. A piezoelectric sensor generates a measurable electric potential in response to the deformation of the sensing element 54 during the contraction cycle of the heart. The amount of voltage generated correlates to the change between the maximum coronary vein diameter $D_{max}$ (i.e., the diameter at the end of systole) and minimum coronary vein diameter $D_{min}$ (i.e., the diameter at the end of diastole), and can be used to estimate cardiac hemodynamic function.

According to some embodiments, the piezoelectric sensor includes patch or disc made of a piezoelectric material coupled to at least one lead. The lead is operably coupled to the processor located within the pulse generator, and is adapted to send a signal indicative of an electric potential generated in response to the deformation of the sensing element. The piezoelectric material can be either a ceramic or a polymeric material. The piezoelectric materials include spatially separated positive and negative charges resulting in electric field, and therefore an electric potential. In response to an applied mechanical stress, such as deformation of the strain sensing element 54, charge separation occurs across the patch or disc and an electric potential is generated.

In the embodiment shown in FIG. 2A, the strain sensing element 54 is coupled to the lead body 35 proximal to the distal tip of the lead, while in the embodiments shown in FIG. 2B, the strain sensing element 54 extends distally from the distal-most portion of the lead 14. In various embodiments, the lead 14 may include additional strain sensing elements located at selected positions along the lead body 35 to facilitate measuring diametrical changes in other portions of the coronary vein 34 or in other coronary veins entirely, e.g., the coronary sinus 31 (see FIG. 1). In the embodiment illustrated in FIG. 2A, only the distal end of the strain sensing element 54 is attached to the leady body 35 at other locations along the strain sensing element 54 in addition to or in lieu of the distal end.

Similarly, in some embodiments, other sensing elements, such as a hemodynamic sensor, may be incorporated into the same lead. In various embodiments, the lead 14 may also be configured to sense localized volume changes in the coronary vein 34 during the cardiac cycle, such as is described in co-pending and commonly assigned U.S. patent application Ser. No. 12/256,203, titled Coronary Vein Hemodynamic Sensor, filed on Oct. 22, 2008, which is incorporated herein by reference in its entirety. In still other embodiments, the lead 14 also includes additional sensors for sensing other physiologic parameters, e.g., blood pressure, blood glucose, blood temperature, in addition to the sensing element 54. Additionally, in other embodiments, multiple leads incorporating the different types of dimensional parameter sensing elements may be employed in a single cardiac rhythm management system.

In one embodiment, the strain sensing element 54 is self-expanding to assume its radially expanded state. In such an embodiment, the strain sensing element 54 may be retained in a radially compressed configuration (not shown) for delivery, e.g., using a delivery catheter or sheath, and may be pre-biased to expand radially into its implanted configuration when released from the catheter or sheath. Of course, any technique, whether now known or later developed, for releasably retaining the strain sensing element 54 in its compressed configuration may be utilized. By way of example only, in one embodiment, the lead 14 may include a dissolvable coating or covering over the strain sensing element 54 which is configured to dissolve in when exposed for a sufficient duration to bodily fluids. When the coating dissolves, the strain sensing element 54 is released to expand to its radially expanded configuration. In other embodiments, the strain sensing element 54 is not self-expanding, and is instead actuated using techniques known in the art, e.g., those utilized to activate balloon-expanded stents and the like.

Figure 3:
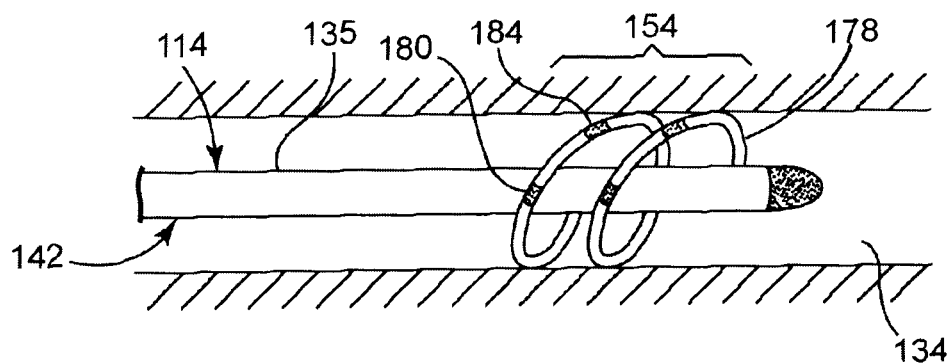
FIG. 3 is a schematic view of a distal portion of the lead positioned in a coronary vein according to another embodiment of the present invention.

FIG. 3 is a schematic view of a distal end portion 142 of a lead body 135 positioned in a coronary vein 134 according to other embodiments of the present invention. According to some embodiments, as shown in FIG. 3, the strain sensing element 154 includes a radially-expandable coil member 178 and at least one pair of longitudinally-spaced electrodes 180, 184 located on the coil member 178. As will be appreciated, the electrodes 180, 184 are electrically isolated from one another, and are each electrically coupled to a separate contact at the proximal end of the lead body 135. The electrodes 180, 184 are further electrically coupled to a processor and/or circuitry within the pulse generator 12 (see FIG. 1) for facilitating sensing and measuring dimensional parameters of the coronary vein 134, for sensing cardiac electrical activity, and/or providing an electrical stimulus to the cardiac tissue. As with the strain sensing element 154 described above, the expandable coil 178 is configured, in various embodiments, to radially expand to bear against and frictionally engage the inner wall of the coronary vein 143 so as to also operate as a fixation mechanism. According to one embodiment, the coil member 178 is coupled to the lead body 135. According to another embodiment, the expandable coil 178 is made integral with the lead body 135.

According to one exemplary embodiment, the electrodes 180, 184 are utilized to sense the localized impedance within the portion of the coronary vein 134 in which they are implanted. In one embodiment, an electrical current is sent from the pulse generator 12 (see FIG. 1) to one of the electrodes 180 or 184, and the resulting electric field is sensed by the other electrode 184 or 180, thus generating a signal from which the pulse generator can measure the localized impedance within the coronary vein 34 adjacent the electrodes 180, 184. Localized impedance within the coronary vein 134 will change generally proportionately with changes in the inner diameter of the coronary vein 134 during the cardiac cycle. Thus, by measuring impedance within the coronary vein 134 across the electrodes 180, 184 substantially continuously during the cardiac cycle utilizing the lead 114, changes in the inner diameter of the coronary vein 134 during the cardiac cycle can be estimated. Additionally, the changes in coronary vein diameter during the cardiac cycle, and in particular, the difference $\Delta D_{max-min}$ between the systolic inner diameter $D_{max}$ and the diastolic inner diameter $D_{min}$ of the coronary vein 134 can be used to estimate and monitor cardiac hemodynamic performance.

Figure 4:
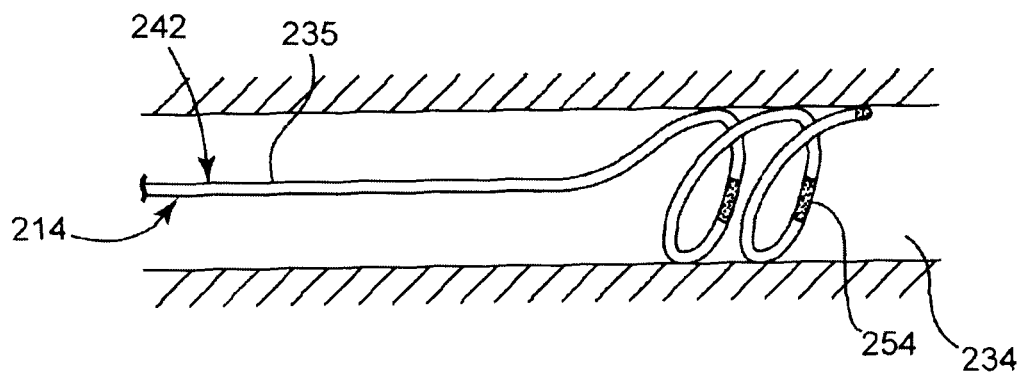
FIG. 4 is a schematic view of a distal portion of the lead positioned in a coronary vein according to yet another embodiment of the present invention.

FIG. 4 is a schematic view of a distal end portion 242 of a lead 214 including at least one strain sensing element 254 according to other embodiments of the present invention. As shown in FIG. 4, the distal end portion 242 has a pre-formed helical shape configured to bear against and frictionally engage the inner wall of the coronary vein 234, securing and stabilizing the distal end 242 of the lead 214 in the coronary vein 234. According to some embodiments, the strain sensing element 254 is incorporated within the helical distal end portion 242. The strain sensing element 254 can include any of the strain sensing elements as described above.

Figure 5:
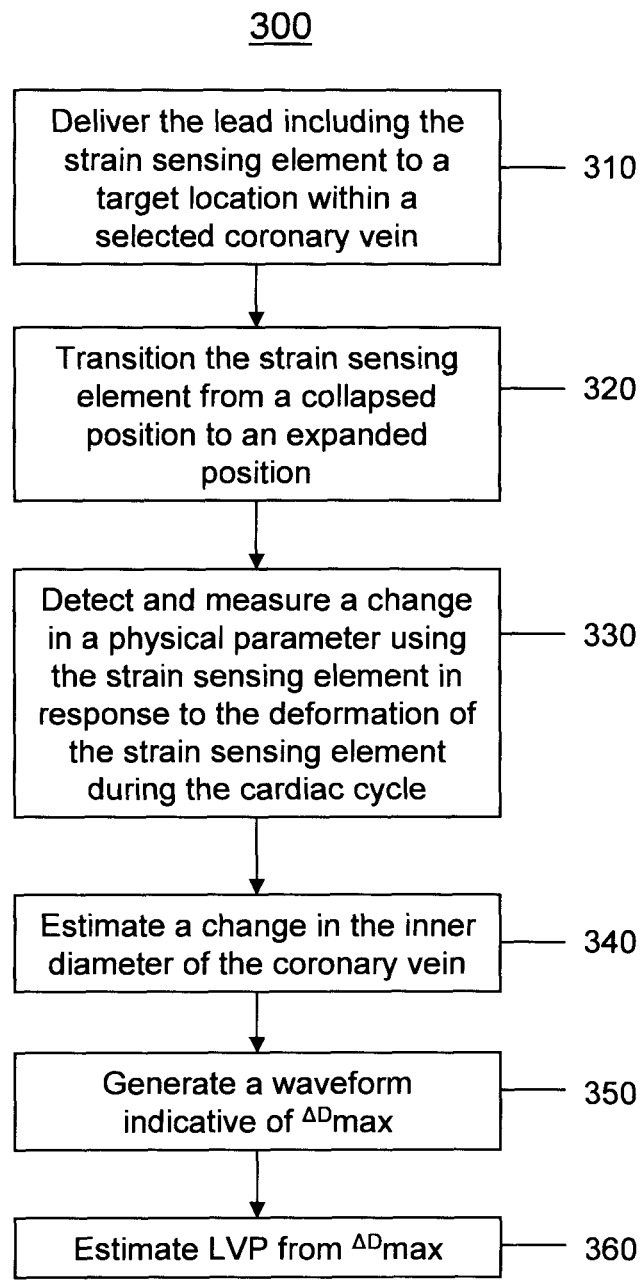
FIG. 5 is a flow chart of a method of estimating cardiac hemodynamic performance according to one embodiment of the present invention.

FIG. 5 is a flow chart of a method (300) of estimating cardiac hemodynamic performance utilizing the cardiac rhythm management system according to one embodiment of the present invention. As shown in FIG. 5, the cardiac rhythm management system, in particular, the pulse generator and the lead are implanted in the patient according to methods known in the art. Accordingly, as part of this process, the lead is delivered to a target location within a coronary vein where the distal end portion of the lead is secured and stabilized within the selected coronary vein (block 310). When the lead is positioned as desired, the strain sensing element is caused or allowed to expand so as to bear against and frictionally engage the inner wall of the coronary vein (block 320). In one embodiment, the strain sensing element is self-expanding to assume its radially expanded state. In such an embodiment, the strain sensing element may be maintained in a collapsed state (e.g., by means of a retaining sheath positioned over the strain sensing element) during delivery of the lead to the desired implantation site. Alternatively, as discussed above, the strain sensing element could be expanded using techniques such as those utilized to activate balloon-expanded stents. Still alternatively, when the lead 214 is utilized, the pre-formed distal end portion 242 allowed to expand to its pre-formed shape so as to contact and frictionally engage the inner wall of the coronary vein.

Once the distal end portion of the lead has been secured and stabilized within the coronary vein, the strain sensing element can be used to detect and measure changes in a physical parameter in response to the deformation of the strain sensing element during the cardiac cycle (block 330). According to one embodiment, the strain sensing element detects and measures a change in electrical resistance in response to the deformation of the strain sensing element. According to another embodiment, the strain sensing element detects and measures a change in electric potential. According to another embodiment, the strain sensing element detects and measures a change in refractive index. According to yet another embodiment, the strain sensor detects and measures change in electrical impedance.

The information is relayed to a signal processor in the pulse generator. The signal processor in the pulse generator uses the information from the strain sensing element to determine a change in the inner diameter $\Delta D_{max}$ of the coronary vein throughout the cardiac cycle (block 340). From this data, a waveform can be generated showing the change in inner diameter of the coronary vein over a specified period of time. (block 350). Changes in left ventricular hemodynamic function, such as $\Delta$LVP, $\Delta$LVEDP, $\Delta$LVESP, $\Delta$dP/dt, etc, can be estimated by evaluating the information collected and processed by the pulse generator (block 360).

Calibration of the hemodynamic performance monitoring system may be performed at implant or thereafter using any temporary invasive or non-invasive technique, e.g., echo, pulse pressure, and the like. In various embodiments, calibration may be performed using an external blood pressure cuff. In one embodiment, an external blood pressure measurement means, e.g., blood pressure cuff, may be used in combination with an advanced patient management system. By way of illustration only, and without limitation, one exemplary such system is the LATITUDE® Patient Management system provided by Boston Scientific Corporation. With such a system, a patient may routinely perform blood pressure checks using an external blood pressure cuff or other non-invasive device. The blood pressure data may then be communicated to the patient management system where it can be stored and also communicated back to the implanted pulse generator 12. Non-invasive arterial systolic and diastolic external blood pressure measurements may then be coordinated, e.g., based on time stamps, with the implanted impedance sensor recordings, and a two-point calibration process may then be performed based on these values. The calibration process may be repeated whenever the patient captures new blood pressure recordings. Of course, other embodiments may utilize different calibration techniques.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A cardiac rhythm management system comprising:
    a cardiac lead adapted to be delivered to a target location within a coronary vein having an inner wall, the cardiac lead including: an elongated lead body including a distal end; a first electrode coupled to the lead body; a second electrode coupled to the lead body; and at least one conductor extending within the lead body operatively coupled to at least one of the first electrode and the second electrode;
    a strain sensing element coupled to the distal end of the lead body and disposed apart from the first electrode and the second electrode, the strain sensing element configured to radially expand against and frictionally engage the inner wall of the coronary vein, and further configured to generate an output signal indicative of changes in a localized inner dimension of the coronary vein during a cardiac cycle; and
    a pulse generator including a processor operatively coupled to the strain sensing element, the processor configured to receive the output signal from the strain sensing element and to estimate a measure of hemodynamic performance therefrom,
    wherein the localized inner dimension is an inner diameter of a portion of the coronary vein, and wherein the processor is configured to calculate a difference $\Delta D_{max-min}$ between a maximum inner diameter and a minimum inner diameter of the portion of the coronary vein during the cardiac cycle and to estimate the measure of hemodynamic performance based on $\Delta_{Dmax-min}$.

2. The cardiac rhythm management system of claim 1 wherein the strain sensing element is operable as a fixation mechanism for chronically securing and stabilizing the distal end of the lead within the coronary vein.

3. The cardiac rhythm management system of claim 1 wherein the strain sensing element is configured to deform in response to the changes in the inner dimension of the coronary vein during the cardiac cycle, and wherein the output signal is proportional to the deformation of the strain sensing element.

4. The cardiac rhythm management system of claim 3 wherein the inner dimension is a localized inner diameter of the coronary vein.

5. The cardiac rhythm management system according to claim 1, wherein the strain sensing element includes a strain gauge sensor.

6. The cardiac rhythm management system according to claim 1, wherein the strain sensing element includes an optical sensor.

7. The cardiac rhythm management system according to claim 1, wherein the strain sensing element includes a piezoelectric sensor.

8. The cardiac rhythm management system of claim 1, wherein the processor is configured to measure the maximum inner diameter of the portion of the coronary vein at an ejection phase of a systolic period of the cardiac cycle and to measure the minimum diameter of the portion of the coronary vein at an end diastolic period of the cardiac cycle based on the output signal from the strain sensing element.

9. A cardiac rhythm management system comprising:
    a cardiac lead adapted to be delivered to a target location within a coronary vein having an inner wall, the cardiac lead including: an elongated lead body including a distal end; a first electrode coupled to the lead body; a second electrode coupled to the lead body; and at least one conductor extending within the lead body operatively coupled to at least one of the first electrode and the second electrode;
    a strain sensing element coupled to the distal end of the lead body, the strain sensing element including an expandable member disposed apart from the first electrode and the second electrode and a strain sensor coupled to the expandable member, the expandable member configured to radially expand against and frictionally engage the inner wall of the coronary vein, the strain sensor configured to generate an output signal indicative of changes in a localized inner dimension of the coronary vein during a cardiac cycle; and
    a pulse generator including a processor operatively coupled to the strain sensing element, the processor configured to receive the output signal from the strain sensing element and to estimate a measure of hemodynamic performance therefrom,
    wherein the localized inner dimension is an inner diameter of a portion of the coronary vein, and wherein the processor is configured to calculate a difference $\Delta D_{max-min}$ between a maximum inner diameter and a minimum inner diameter of the portion of the coronary vein during the cardiac cycle and to estimate the measure of hemodynamic performance based on $\Delta_{Dmax-min}$.

10. The cardiac rhythm management system according to claim 9, wherein the strain sensor comprises a strain gauge sensor, an optical sensor or a piezoelectric sensor.

11. The cardiac rhythm management system according to claim 9, wherein the expandable member has a helical expanded configuration.

12. The cardiac rhythm management system according to claim 9, wherein the expandable member comprises a shape memory material.

* * * * *